(12) United States Patent
Tang et al.

(10) Patent No.: US 10,525,292 B2
(45) Date of Patent: Jan. 7, 2020

(54) RESPIRATORY DEVICE WITH UNIDIRECTIONAL VALVE FOR ATTACHING ACTIVE VENTING SYSTEM

(71) Applicant: INNOSPARKS PTE LTD, Singapore (SG)

(72) Inventors: Ee Ho Tang, Singapore (SG); Kwok Jiang Sak, Singapore (SG); Jerome Wei Liang Lee, Singapore (SG)

(73) Assignee: INNOSPARKS PTE LTD, Singapore (SG)

( * ) Notice: Subject to any disclaimer, the term of this patent is extended or adjusted under 35 U.S.C. 154(b) by 511 days.

(21) Appl. No.: 15/301,561

(22) PCT Filed: May 26, 2014

(86) PCT No.: PCT/SG2014/000228
§ 371 (c)(1),
(2) Date: Oct. 3, 2016

(87) PCT Pub. No.: WO2015/183177
PCT Pub. Date: Dec. 3, 2015

(65) Prior Publication Data
US 2017/0120084 A1    May 4, 2017

(51) Int. Cl.
*A62B 18/10* (2006.01)
*A61M 16/20* (2006.01)
(Continued)

(52) U.S. Cl.
CPC ......... *A62B 18/006* (2013.01); *A61M 16/208* (2013.01); *A62B 9/04* (2013.01); *A62B 18/02* (2013.01); *A62B 18/10* (2013.01)

(58) Field of Classification Search
CPC .............. A61M 16/0066; A61M 16/10; A61M 16/106; A61M 2205/502;
(Continued)

(56) References Cited

U.S. PATENT DOCUMENTS 4,414,973 A * 11/1983 Matheson .............. A62B 18/00
128/206.15
7,066,177 B2    6/2006 Pittaway
(Continued)

FOREIGN PATENT DOCUMENTS

CN    102319491 A    1/2012
EP    1854494 A1    11/2007
(Continued)

OTHER PUBLICATIONS

Japanese Office Action for corresponding application No. 2016-568832; dated Oct. 18, 2017.
(Continued)

*Primary Examiner* — Annette Dixon
(74) *Attorney, Agent, or Firm* — Cantor Colburn LLP (57) ABSTRACT

Discloses a respiratory device comprising a mask positioned around the mouth and nose of a wearer to form a relative closed area sealed from the ambient air, at least one unidirectional valve for mounting of an active venting system, installed onto the mask for exhausting warm, moist exhaled air from the interior space of the respirators and at least one active venting system attached onto the valve and operated during the exhalation cycle. The top housing of the unidirectional valve has an attachment member for attaching the active venting system onto it. The active venting system can be attachable or detachable onto the valve. The valve attached with active venting system together effectively and quickly exchanges the air from the interior of the mask during exhalation cycle. When the AVS is not attached onto the valve, a simple valve cap can be attached on instead, for aesthetic purposes.

14 Claims, 10 Drawing Sheets

(51) Int. Cl.
*A62B 18/00* (2006.01)
*A62B 9/04* (2006.01)
*A62B 18/02* (2006.01)

(58) Field of Classification Search
CPC ........... A61M 2205/8206; A62B 18/00; A62B 18/003; A62B 18/006; A62B 18/02; A62B 18/025; A62B 18/08; A62B 18/084; A62B 18/10; A62B 23/025; A62B 7/04; A62B 7/10; A62B 9/02; A62B 9/04; F16K 15/148; Y10S 24/53; Y10T 137/789; Y10T 24/45079
See application file for complete search history.

(56) References Cited

U.S. PATENT DOCUMENTS

| | | | |
|---|---|---|---|
| 7,523,755 B2 | 4/2009 | Richardson | |
| 8,689,791 B2 | 4/2014 | Hayek | |
| 2008/0257352 A1* | 10/2008 | Penton | A62B 7/04 128/205.24 |

FOREIGN PATENT DOCUMENTS

| | | | | |
|---|---|---|---|---|
| GB | 2505484 A | 3/2014 | | |
| JP | 2008514302 A | 5/2008 | | |
| JP | 2015530148 A | 10/2015 | | |
| WO | 0170092 A2 | 9/2001 | | |
| WO | 2009066833 A1 | 5/2009 | | |
| WO | 2014035641 A2 | 3/2014 | | |
| WO | WO-2014035641 A2 * | 3/2014 | ........... A62B 18/006 |
| WO | WO-2016181144 A1 * | 11/2016 | ............... A62B 9/04 |

OTHER PUBLICATIONS

European Search Report for corresponding application EP14893428; Report dated Nov. 22, 2017.
International Search Report for corresponding application PCT/SG2014/000228 filed May 26, 2014; dated Feb. 26, 2015.
European Examination Report for corresponding application 14 893 428.4; Report dated Feb. 25, 2019.

* cited by examiner

RESPIRATORY DEVICE WITH UNIDIRECTIONAL VALVE FOR ATTACHING ACTIVE VENTING SYSTEM

CROSS REFERENCE TO RELATED APPLICATION

This application is a U.S. National Phase application under 35 U.S.C. § 371 of International Application No. PCT/SG2014/000228, filed on 26 May 2014 of which the full contents are herein incorporated by reference.

TECHNICAL FIELD

The present disclosure relates generally to respiratory devices. Embodiments of the disclosure are particularly related to unidirectional valve with the feature of enabling active venting system to be attached onto it, for use on a face mask or respirator.

BACKGROUND

Filtering facemasks or respirators are widely used to protect the user from inhaling dust or chemical particles, depending on the filter properties and certifications. However, wearing a respirator for prolonged periods causes discomfort to the user, due to the build-up of hot air, moisture and carbon dioxide within the respirator. As the time progress, the moisture build-up will also block the filter material, making it more difficult for the user to breathe.

To mitigate these issues, unidirectional valves are commonly installed to respirators. There are different types of valve concepts and membranes or flaps used in the respirators. The basic concept is to allow exhausting of warm, moist exhaled air from the interior space of the respirator, when the flap opens upon exhalation. Conversely, the flap closes upon inhalation, preventing ambient air and particles from entering into the interior of the respirator. However, these valves have limited effectiveness and do not allow exhalation to be purged fast enough. This is even more apparent if the internal space of the respirator is large resulting in more dead space, or if the wearer has shallow breathing which may not be strong enough to open the membrane or flap wide.

Most of the respirators are installed with a Powered Air Purifying Respirators (PAPR) comprising a blower for supplying air from the exterior of the respirator into the respirator. Such blowers provide positive air-flow, or supply air to the wearer. Some respiratory device use Active Venting System (AVS) for example, comprising a blower and electronics in a plastic housing, for sucking out warm, moist air from the internal space of respirator. The AVS works differently from PAPR, as it does not supply air into the respirator, but rather sucks air out from the interior of the respirator to provide air exchange.

Thus, the respirators are usually installed with either unidirectional valve or AVS or PAPR systems to allow air exchange inside the respirator. AVS are comfortable under prolong use and suitable for general public compared to PAPR system. The respirator with unidirectional valve alone does not allow exhalation to be purged fast enough. Also, the respirators installed with AVS alone may not prevent ambient air from flowing in, when the AVS runs out of battery and/or stop operating.

A need, therefore, exists for an improved unidirectional valve with the feature of enabling an electronic blower to be attached onto it, to overcome the above drawbacks.

SUMMARY

The following summary is provided to facilitate an understanding of some of the innovative features unique to the disclosed embodiment and is not intended to be a full description. A full appreciation of the various aspects of the embodiments disclosed herein can be gained by taking into consideration the entire specification, claims, drawings, and abstract as a whole.

It is, therefore, one aim of the disclosed embodiments to provide for a respirator device comprising a mask positioned around the mouth and nose of a wearer to form a relative closed area sealed from the ambient air, at least one unidirectional valve for mounting an active venting system, installed onto the mask for exhausting warm, moist exhaled air from the interior space of the respirator and at least one active venting system attachable onto the uni-directional valve and operated during the exhalation cycle. The unidirectional valve has a top housing, a bottom housing, a membrane seat, a membrane pinned at the membrane seat and a first attachment member.

According to an embodiment of the invention, the active venting system consisting of an electronic blower, a power source and a second attachment member. The active venting system is attachable onto the top housing of the unidirectional valve by fixing the second attachment member on the first attachment member.

It is, therefore, one aim of the disclosed embodiments to provide for a respirator device in which the active venting system is detachable from the top housing of the unidirectional valve by unfixing the second attachment member from the first attachment member.

It is, therefore, one aim of the disclosed embodiments to provide for a respirator device in which the bottom and top housing of the unidirectional valve are injection molded, fused together and then installed onto the respirator.

It is, therefore, one another aim of the disclosed embodiments to provide for a respirator device in which the top housing of the unidirectional valve has a plurality of supporting pillars extending from the circumference of the top housing towards a center pillar. The center pillar extends from the lower center of the top housing to the center of the bottom housing.

It is, therefore, one another aim of the disclosed embodiments to provide for a respirator device in which a membrane is placed between the top and bottom housing of the unidirectional valve such that the membrane is pinned at the center between the center pillar and the membrane seat. The active venting system actively sucks out air when the membrane opens within the valve.

It is, therefore, another aim of the disclosed embodiments to provide for a respirator device in which the membrane prevents backflow of ambient air into the mask.

It is, therefore, another aim of the disclosed embodiments to provide for a respirator device in which the membrane prevents backflow of ambient air into the mask for example when the active venting system runs out of battery and/or stop operating.

It is, therefore, one another aim of the disclosed embodiments to provide for a respirator device in which the top housing of the unidirectional valve is covered with a valve cap for aesthetic purpose, when the active venting system is not attached onto the valve.

It is, therefore, one another aim of the disclosed embodiments to provide for a respirator device in which the membrane of the unidirectional valve is pegged in the middle. The membrane opens all around the circumference of the valve during exhalation cycle to exhaust warm, moist exhaled air from the interior space of the respirator.

It is, therefore, one another aim of the disclosed embodiments to provide for a respirator device in which the attachment member of AVS has at least one locking teeth and the attachment member of unidirectional valve has at least one groove for receiving at least one locking teeth at the time of fixing the active venting system.

It is, therefore, one another aim of the disclosed embodiments to provide for a respirator device in which the active venting system is fixed to the unidirectional valve by inserting the locking teeth of the unidirectional valve into the grooves of the AVS and turning the active venting system clockwise. The active venting system is unfixed from the unidirectional valve by turning the active venting system anti-clockwise.

It is, therefore, one another aim of the disclosed embodiments to provide for a respirator device in which the attachment member comprises magnets and/or snap-fits and the respiratory device can be of disposable or non-disposable type.

It is, therefore, another aim of the disclosed embodiments to provide for a respirator device in which the valve along with the active venting system can effectively and quickly remove the exhaled air in case if the internal space of the respirator is large resulting in more dead space, or if the wearer has shallow breathing which may not be strong enough to open the membrane or the flap wide.

Other aspects and advantages of the invention will become apparent from the following detail description, taken in conjunction with the accompanying drawings, illustrating by way of example the principles of the invention.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein. Moreover, those in the art will understand that the drawings are not to scale. Wherever possible, like elements have been indicated by identical numbers.

DETAILED DESCRIPTION OF ILLUSTRATIVE EMBODIMENTS

The particular values and configurations discussed in these non-limiting examples can be varied and are cited merely to illustrate at least one embodiment and are not intended to limit the scope thereof.

A respiratory device comprising a mask positioned around the mouth and nose of a wearer to form a relative closed area sealed from ambient air, at least one unidirectional valve installed onto the mask for exhausting warm, moist exhaled air from the interior space of the respirators and at least one active venting system attached onto the valve, operated during the exhalation cycle is disclosed. The top housing of the unidirectional valve has an attachment member for attaching the active venting system. The active venting system can be attachable or detachable onto the valve. The valve attached with active venting system together effectively and quickly exchanges the air from the interior of the mask during exhalation cycle. When the AVS is not attached onto the valve, a simple valve cap can be attached on instead, for aesthetic purposes.

Referring to FIGS. 1-4 a unidirectional valve 100 for use in a respiratory device is disclosed. The valve 100 has a top housing 108, a bottom housing 110, a membrane 114, at least one first attachment member 102, a membrane seat 116, a center pillar 106 and at least one supporting pillar 104 extending from the circumference of the valve 100 to the center pillar 106. The unidirectional valve 100 acts as a two-in-one valve. One purpose of the valve 100 is to act as a unidirectional valve for venting out warm, moist air from the internal space of respirators through the membrane 114 (shown in FIG. 4). The other purpose of the valve 100 is to allow the Active Venting System (AVS) to be attached onto it for effectively and quickly removing the warm, moist air from the internal space of respirators.

Figure 1:
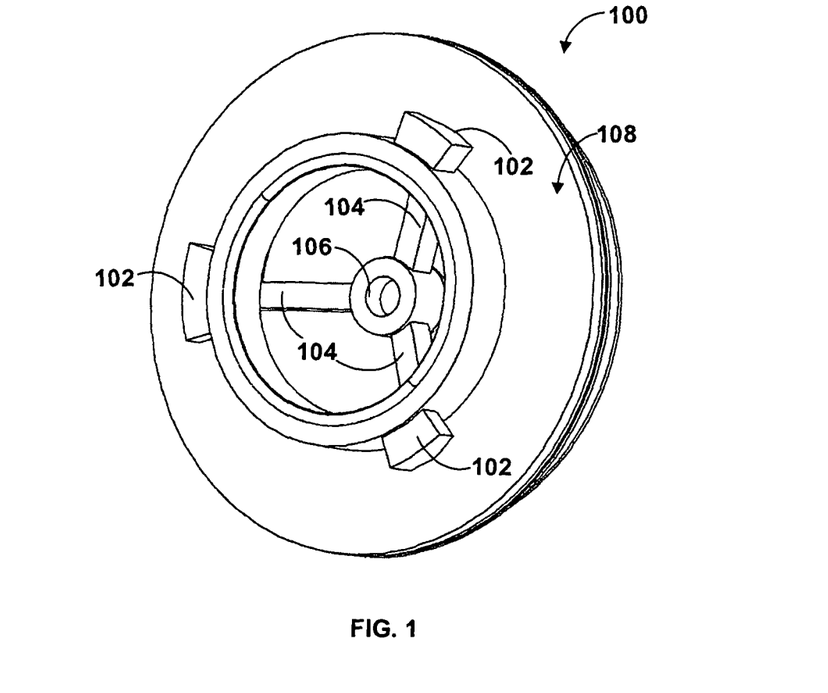
FIG. 1 is an illustration of a perspective view of a unidirectional valve, in accordance with the disclosed embodiment.
Figure 2:
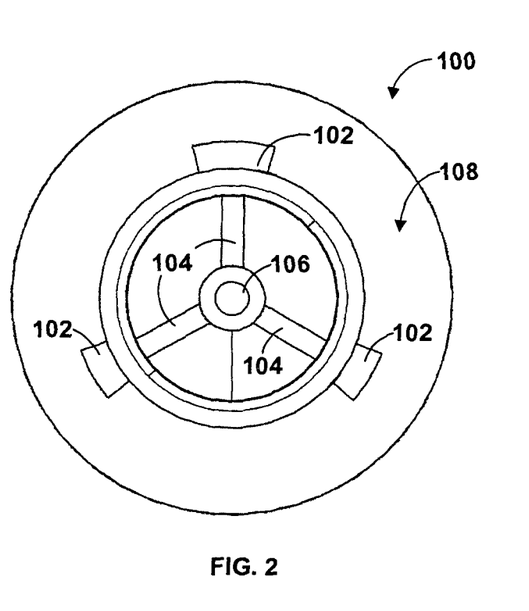
FIG. 2 is an illustration of a top view of the unidirectional valve depicted in FIG. 1, in accordance with the disclosed embodiment.
Figure 3:
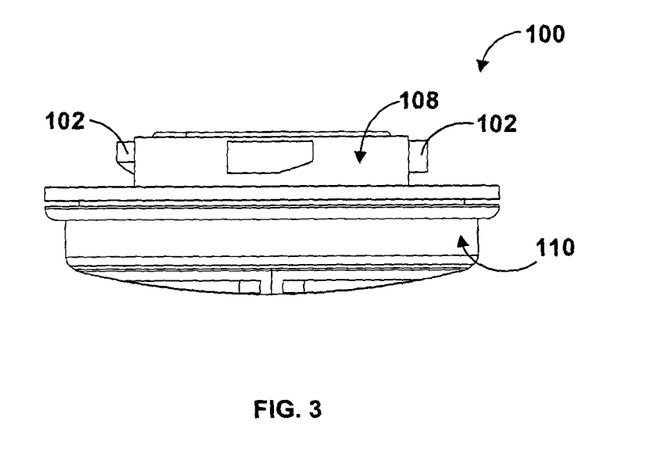
FIG. 3 is an illustration of a side view of the unidirectional valve depicted in FIG. 1, in accordance with the disclosed embodiment.
Figure 4:
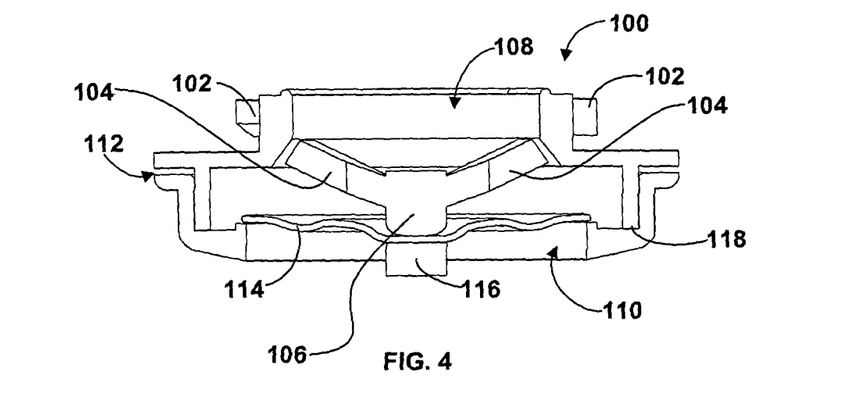
FIG. 4 an illustration a cross sectional view of the unidirectional valve depicted in FIG. 3, in accordance with the disclosed embodiment.

FIGS. 3-4 show one embodiment of the valve 100 having the top housing 108 and the bottom housing 110. The top housing 108 has one or more first attachment member 102 for example, one or more locking teeth and one or more supporting pillars 104 extending from the circumference of the top housing 108 to the center pillar 106. The top housing 108 and the bottom housing 110 can be injection molded and are installed onto the respirator through a variety of means. The most common method of installing the housing on the respirator is ultrasonic heat fusing but other fusion method can also be used without limitation. It should be noted that the most ideal valve shape is circular, but can be in other shapes such as rectangular, oval, etc, and is not limited to being circular. The shape and type of the attachment member 102 is adapted for attaching the AVS and may vary according to the shape of the valve 100.

The top housing 108 is specially designed such that it can attach the AVS onto it. The first attachment member 102 can be for example two to four locking teeth or other means utilized for attaching the AVS onto the valve. 100, such as magnets or snap-fits, etc, without limitation. The AVS may comprise of a blower and electronics in a plastic housing. The AVS can be attached to the valve 100 to effectively and quickly suck out warm, moist air from the internal space of respirators through the unidirectional valve 100.

The center pillar 106 extends from the lower center of the top housing 108 to the center of the bottom housing 110. The membrane 114 is placed between the top housing 108 and bottom housing 110 and pinned at the center between the center pillar 106 and the membrane seat 116 as shown in FIG. 4. When the AVS (shown in FIG. 5) is attached onto the valve 100, the active venting system actively sucks out air when the membrane 114 is opened. In one embodiment of the invention, the membrane 114 prevents backflow of ambient air into the mask and thus acts a unidirectional valve 100. In other embodiment of the invention, the membrane 114 prevents backflow of ambient air into the mask for example when the active venting system runs out of battery and/or stop operating.

It should be noted that the membrane 114 of the unidirectional valve 100 is pegged in the middle. The membrane 114 opens all around the circumference of the valve 100 during exhalation cycle to exhaust warm, moist exhaled air from the interior space of the respirators. The bottom and top housings 108 and 110 are injection molded, fused together at a portion 118 and then installed onto the respirator as shown in FIG. 4. A gap 112 shown in FIG. 4 is utilized for attaching the valve and the respirator/mask.

The AVS has an electronic fan for sucking the exhaled air from the mask. The AVS 200 also has at least one second attachment member 204 for fixing and unfixing the AVS 200 onto the first attachment member 102 of the valve 100. At the time of fixing the active venting system 200 onto the valve 100, the second attachment member 204 for example, having at least one groove receives at least one first attachment member 102 for example, comprising at least one locking teeth.

Figure 5:
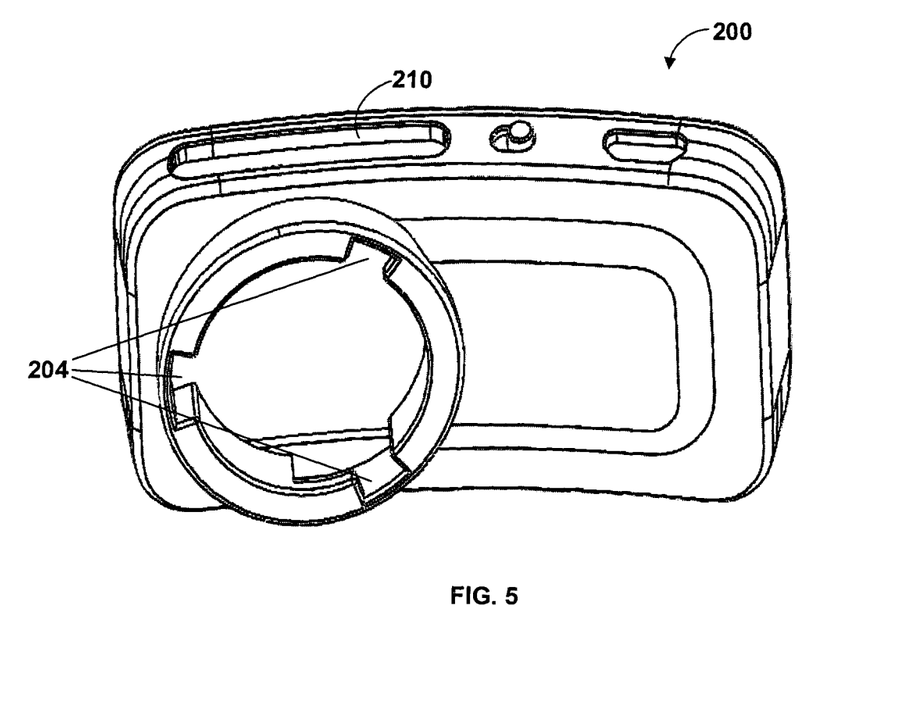
FIG. 5 is an illustration of a perspective view of an active venting system, in accordance with the disclosed embodiment.
Figure 6:
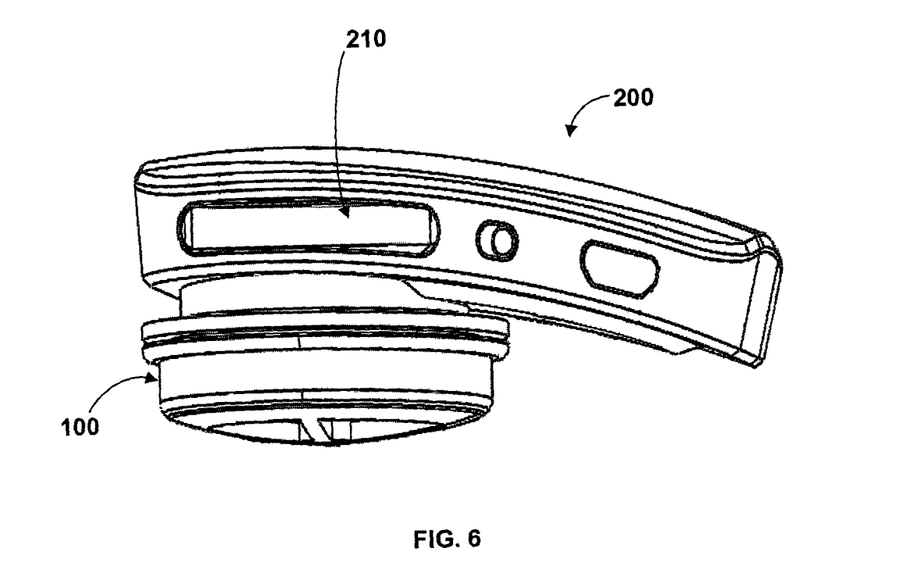
FIG. 6 is an illustration of a side view of the unidirectional valve depicted in FIG. 1 attached with the active venting system depicted in FIG. 5, in accordance with the disclosed embodiment.
Figure 7:
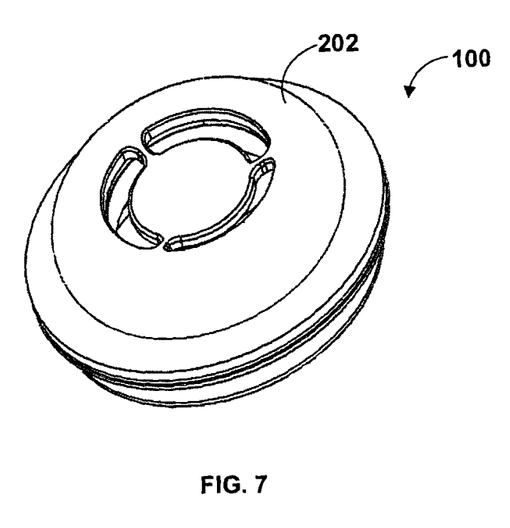
FIG. 7 is an illustration of a side view of the unidirectional valve depicted in FIG. 1 attached with a valve cap, in accordance with the disclosed embodiment.

FIG. 5 shows the AVS 200 with the second attachment member 204 having at least one groove for attaching onto the valve 100. FIG. 6 illustrates the active venting system 200 fixed onto the valve 100 depicted in FIGS. 1-4. The active venting system 200 is fixed onto the unidirectional valve 100 by inserting the locking teeth of the unidirectional valve 100 and turning the active venting system 200 clockwise. It should be noted that the blower inside the AVS 200 sucks air inside the mask when the membrane 114 is opened and delivers it to outside atmosphere through the blower outlet 210. The active venting system 200 is unfixed from the unidirectional valve 100 by turning the active venting system 200 anti-clockwise. As shown in FIG. 7, the top housing 108 of the unidirectional valve 100 depicted in FIGS. 1-4 is covered with a valve cap 202 for aesthetic purpose, when the active venting system 200 is not attached onto the valve 100.

Figure 8:
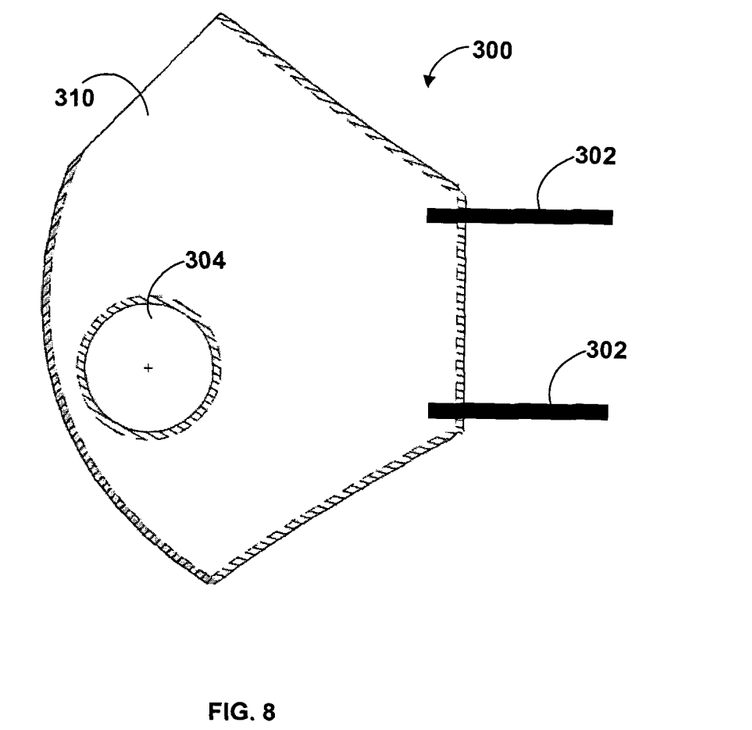
FIG. 8 is an illustration of a side view of a foldable disposable respirator showing a hole for attaching the unidirectional valve, in accordance with the disclosed embodiment.
Figure 9:
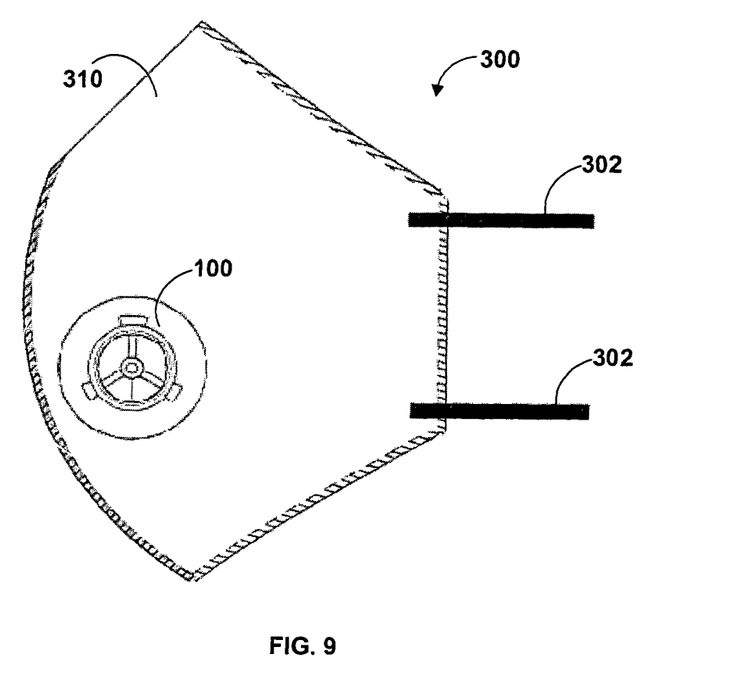
FIG. 9 is an illustration of a side view of a foldable disposable respirator with unidirectional valve depicted in FIG. 1 installed on the hole depicted FIG. 8, in accordance with the disclosed embodiment.

FIG. 8 is an illustration of a side view of a foldable disposable respirator 300 showing a hole 304 for installing the unidirectional valve 100, in accordance with the disclosed embodiment. FIG. 9 shows, the unidirectional valve 100 depicted in FIG. 1 installed in the hole 304 depicted in FIG. 8 of the respirator 300. The bottom housing 110 of the valve 100 depicted in FIG. 3 can be injection molded and installed onto the hole 304 of the respirator 300 through a variety of means, such as ultrasonic heat fusing. The most ideal valve shape is circular, but can be in other shapes such as rectangular and is not limited to being circular. It should be noted that the hole 304 and bottom housing 110 can take any shape and for simplicity the circular hole 304 for the unidirectional valve 100 is shown in FIGS. 8-9.

Figure 10:
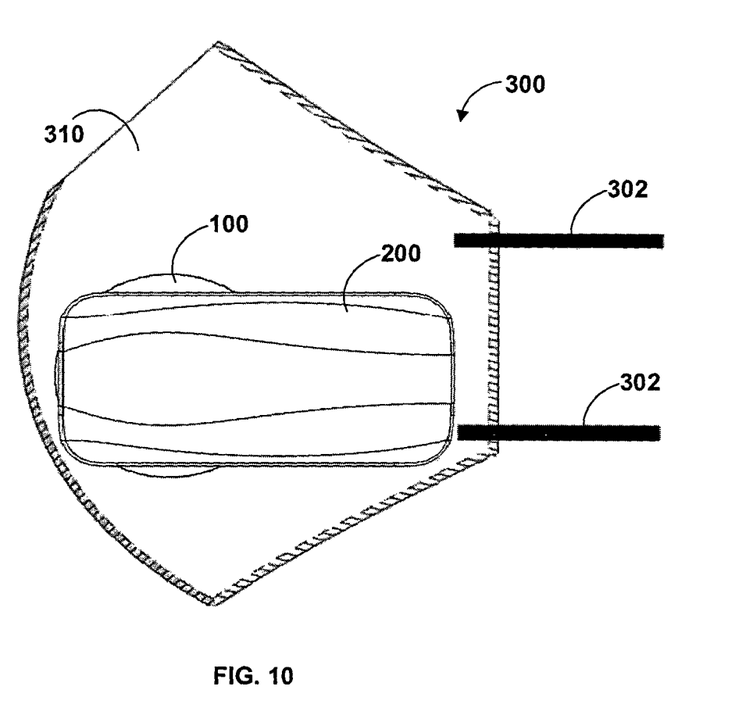
FIG. 10 is an illustration of a side view of a foldable disposable respirator with active venting system attached onto the unidirectional valve, in accordance with the disclosed embodiment.

The AVS 200 depicted in FIG. 5 can be attached to the top housing 108 of the valve 100 as shown in FIG. 10. The first attachment member 102 of the valve 100 is fixed with the second attachment member 204 of the AVS 200. During exhalation cycle, the unidirectional valve 100 with the AVS 200 effectively and quickly sucks the warm air inside the mask 310. The electronic blower sucks the warm air inside the mask 310 and is delivered outside the atmosphere through the blower outlet 210, which is shown in FIG. 5. The membrane 114 is unidirectional and thus allows only air from interior of the mask 310 to the atmosphere and works only during exhalation cycle. During inhalation cycle, the membrane 114 is impermeable to the air and does not allow air inside the mask 310. A common attaching mechanism is using two to four locking teeth. This allows the AVS 200 to be easily attached or detached by aligning the locking teeth and turning in clockwise or anti-clockwise direction. There may also be other forms of attaching and locking mechanism possible for people skilled in the art, such as using magnets or snap-fits.

Figure 11:
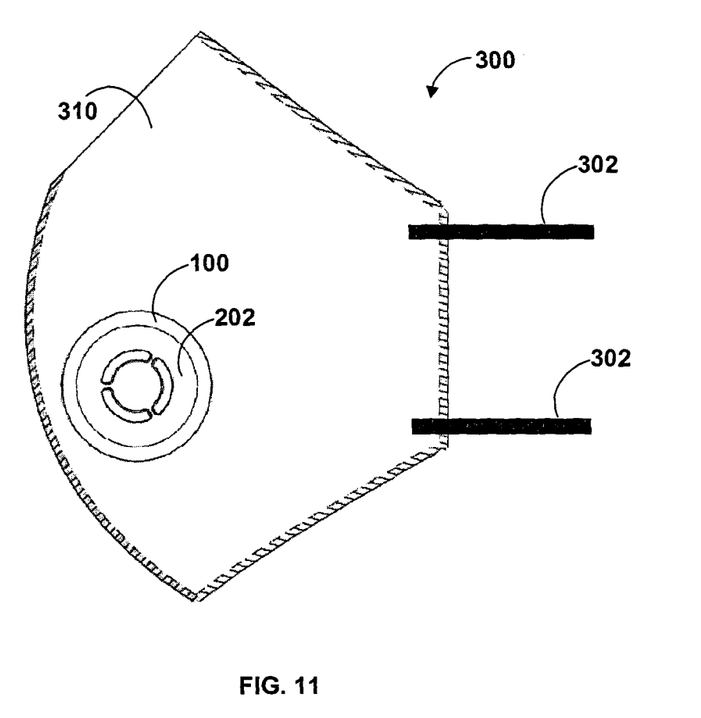
FIG. 11 is an illustration of a side view of a foldable disposable respirator with valve cap depicted in FIG. 7 attached on the unidirectional valve, in accordance with the disclosed embodiment.

Referring to FIG. 11, when the AVS 200 is not attached onto the valve 100, a simple valve cap 202 can be attached instead, for aesthetic purposes. For example, when the active venting system 200 runs out of battery and/or stop operating, it can be unfixed from the unidirectional valve 100 by turning it anti-clockwise. Then, a valve cap 202 can be attached onto the valve 100. The valve cap 202 can take the shape of the valve 100, for example, as shown in FIGS. 8 and 11, the valve cap 202 and the valve 100 are circular in shape. The respirator 300 can be either of the disposable or non-disposable types, such as foldable disposable respirator or full face filtering respirator without limitation. FIGS. 8-11 are explained with respirator 300 of foldable disposable type. Also, as shown in FIGS. 8-11, the wearer can use a pair of latch 302 to firmly wear the respirator 300 on his/her face. The latch 302 can be of any suitable material that can be utilized as a fastener. The latch 302 can also be of adjustable type to suit wearer of various facial features.

It should be noted that the respirator can be used with or without the AVS. In both cases, the respirator is able to allow unidirectional airflow from the internal space of the respirator, and hence meet certification standards such as N95 set by National Institute for Occupational Safety and Health (NIOSH). With the AVS in operation, the respirator actively sucks out air through the open membrane within the valve. The membrane prevents backflow of ambient air into the respirator in the event that the wearer's inhalation is too heavy, or if the AVS runs out of battery and/or stop operating.

Through the above description, one can understand that the respiratory device with active venting system attachable on the valve can effectively and quickly discharge exhaled air and vent the mask in every breathing cycle. All these features will provide wearers with an improved breathe experience due to the active air exchange within the mask. The unidirectional valves along with the AVS effectively and quickly improve the air exchange compared to individual use of unidirectional valve or AVS.

It will be appreciated that variations of the above disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Although embodiments of the current disclosure have been described comprehensively, in considerable detail to cover the possible aspects, those skilled in the art would recognize that other versions of the disclosure are also possible.

What is claimed is:

1. A respiratory device, comprising:
   a mask adapted to create a substantially air tight seal around the nose and mouth of a person;
   a unidirectional valve for exhausting exhaled air from the interior of said respiratory device that includes a top housing, a bottom housing, a membrane seat, a membrane pinned at the membrane seat and a first attachment member;
   wherein the top housing has a plurality of supporting pillars extending from the circumference of the top housing towards a center pillar; wherein the center pillar extends from the lower center of the top housing to the center of the bottom housing; wherein the membrane is placed between the top and bottom housing such that the membrane is pinned at the center between the center pillar and the membrane seat;
   and
   a detachable venting system that includes an electronic blower, a power source, a second attachment member;
   wherein said detachable venting system can be connected and disconnected to said first attachment member of said unidirectional valve.

2. The respiratory device of claim 1, wherein said detachable venting system is an Active Venting System that operates during exhalation cycle.

3. The respiratory device of claim 2 which can be used with Active Venting System when said Active Venting System is connected and without Active Venting System when said Active Venting System is not connected.

4. The respiratory device of claim 2, wherein the second attachment member has at least one locking tooth and the first attachment member has at least one groove for receiving at least one locking tooth.

5. The respiratory device of claim 4, wherein the venting system is fixed to the unidirectional valve by inserting its groove into the locking tooth of the unidirectional valve and turning the active venting system clockwise.

6. The respiratory device of claim 4, wherein the venting system is unfixed from the unidirectional valve by turning the active venting system anti-clockwise.

7. The respiratory device of claim 2, wherein the first and second attachment member comprises magnets and/or snap-fits.

8. The respiratory device of claim 1, wherein the bottom and top housing are injection molded, fused together and then installed onto the respiratory device.

9. The respiratory device of claim 1, wherein the membrane opens all around the circumference of the valve during exhalation cycle to exhaust warm, moist exhaled air from the interior space of the respiratory device.

10. The respiratory device of claim 1 wherein the venting system actively sucks out air when the membrane is opened.

11. The respiratory device of claim 1 wherein the membrane prevents backflow of ambient air into the mask.

12. The respiratory device of claim 1 wherein the membrane prevents backflow of ambient air into the mask when the venting system runs out of the power source and/or stop operating.

13. The respiratory device of claim 1, wherein the top housing of the unidirectional valve is covered with a valve cap for aesthetic purpose.

14. The respiratory device of claim 1, wherein the respiratory device is either disposable or non-disposable.

* * * * *